US011275032B2

(12) United States Patent
Kirchgaessler et al.

(10) Patent No.: US 11,275,032 B2
(45) Date of Patent: Mar. 15, 2022

(54) METHOD OF DETERMINING THE PROPORTION OF CYANIDE IN A SAMPLE

(71) Applicant: CYANOGUARD AG, Waedenswil (CH)

(72) Inventors: Benedikt Fabian Quirin Kirchgaessler, Waedenswil (CH); Marjorie Sonnay, Basel (CH)

(73) Assignee: CYANOGUARD AG, Waedenswil (CH)

( * ) Notice: Subject to any disclaimer, the term of this patent is extended or adjusted under 35 U.S.C. 154(b) by 160 days.

(21) Appl. No.: 16/652,666

(22) PCT Filed: Oct. 2, 2018

(86) PCT No.: PCT/IB2018/057632
§ 371 (c)(1),
(2) Date: Mar. 31, 2020

(87) PCT Pub. No.: WO2019/069220
PCT Pub. Date: Apr. 11, 2019

(65) Prior Publication Data
US 2020/0256803 A1 Aug. 13, 2020

(30) Foreign Application Priority Data

Oct. 3, 2017 (GB) ..................... 1716136

(51) Int. Cl.
*G01N 21/78* (2006.01)
*G01N 31/22* (2006.01)

(52) U.S. Cl.
CPC ............. *G01N 21/78* (2013.01); *G01N 31/22* (2013.01)

(58) Field of Classification Search
CPC ............................ G01N 21/78; G01N 31/22
See application file for complete search history.

(56) References Cited

U.S. PATENT DOCUMENTS 5,612,223 A * 3/1997 Kim ................... G01N 33/5094
424/93.73
5,961,469 A * 10/1999 Roizen ................... G01N 33/84
356/39

(Continued)

FOREIGN PATENT DOCUMENTS

DE 196 08 808 A1 9/1997
WO WO 2011/116006 A2 9/2011

(Continued)

OTHER PUBLICATIONS

Blackledge, et al., "New Faciie Method to Measure Cyanide in Blood", *Anal. Chem.* vol. 82, No. 10, pp. 4216-4221, May 15, 2010.

(Continued)

*Primary Examiner* — Brian R Gordon
*Assistant Examiner* — Dwan A Gerido
(74) *Attorney, Agent, or Firm* — Curatolo Sidoti Co., LPA; Salvatore A. Sidoti; Floyd Trillis, III

(57) ABSTRACT

A method of determining the proportion of cyanide in a sample, comprising the following steps:

(Continued)

*Cyanide Calibration Curve 581/527 nm*

(i) Add the sample to be analysed to a sensor molecule that is selected from cobryrinic acid hepta C1-4 alkyl esters of the Formula I

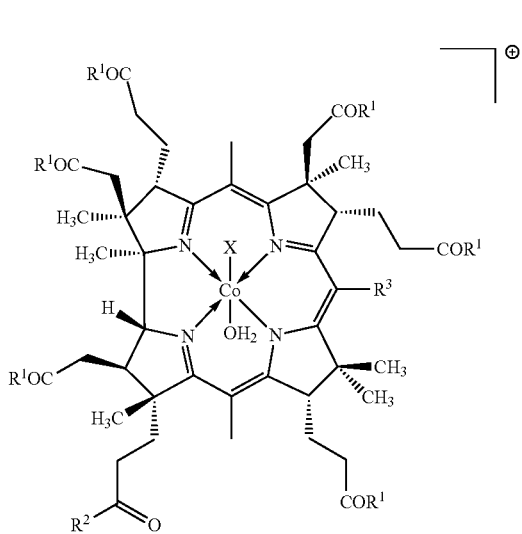

in which X is CN, $R^3$ is H, and $R^1$ and $R^2$ are $OCH_3$;
(ii) Subject the sample to UV-vis spectroscopic analysis in the range 450-700 nm;
(iii) Determine the free cyanide concentration from the equation (i)

$$C=(A-0.058)/0.104 \qquad (i)$$

in which C is the free cyanide concentration and A is $$A=A_{581}/A_{527}$$

the ratio of the absorbances at 581 and 527 nm, the equation (i) having been derived from a calibration curve that is a plot of A ratios calculated at 0-1 mg/L $CN^-$ with a constant 46 nmol of sensor compound.

The method provides a particularly accurate assessment of cyanide concentration in an unknown sample.

1 Claim, 1 Drawing Sheet

(56) References Cited

U.S. PATENT DOCUMENTS

| | | | |
|---|---|---|---|
| 8,741,658 B2* | 6/2014 | Boss | G01N 31/22 436/109 |
| 2013/0344620 A1 | 12/2013 | O'Farrell et al. | |
| 2014/0141522 A1* | 5/2014 | Zelder | C07H 23/00 436/109 |
| 2015/0353590 A1* | 12/2015 | Boss | C07F 15/065 514/185 |

FOREIGN PATENT DOCUMENTS

| | | |
|---|---|---|
| WO | WO 2012/136793 A1 | 10/2012 |
| WO | WO 2015/106071 A1 | 7/2015 |

OTHER PUBLICATIONS

Zelder, et al., "Rapid Visual Detection of Blood Cyanide", *Anal. Methods*, vol. 4, No. 9, pp. 2632-2634, Sep. 2012.
Swezey, et al., "Comparison of a New Cobinamide-Based Method to a Standard Laboratory Method for Measuring Cyanide in Human Blood", *J. Analytical Toxicology*, vol. 37, pp. 382-385, 2013.
Corresponding International Application No. PCT/IB2018/057632—International Search Report, dated Jan. 29, 2019.
Corresponding International Application No. PCT/IB2018/057632—International Written Opinion, dated Jan. 29, 2019.
Corresponding Great Britain Application No. GB 1716136.5—Search Report, dated Jun. 28, 2018.
Hassan S.S.M. et al., "A novel spectrophotometric method for batch and flow injection determination of cyanide in electroplating wastewater", pp. 1088-1095, Talanta, vol. 71 (3), Jul. 24, 2006.

* cited by examiner

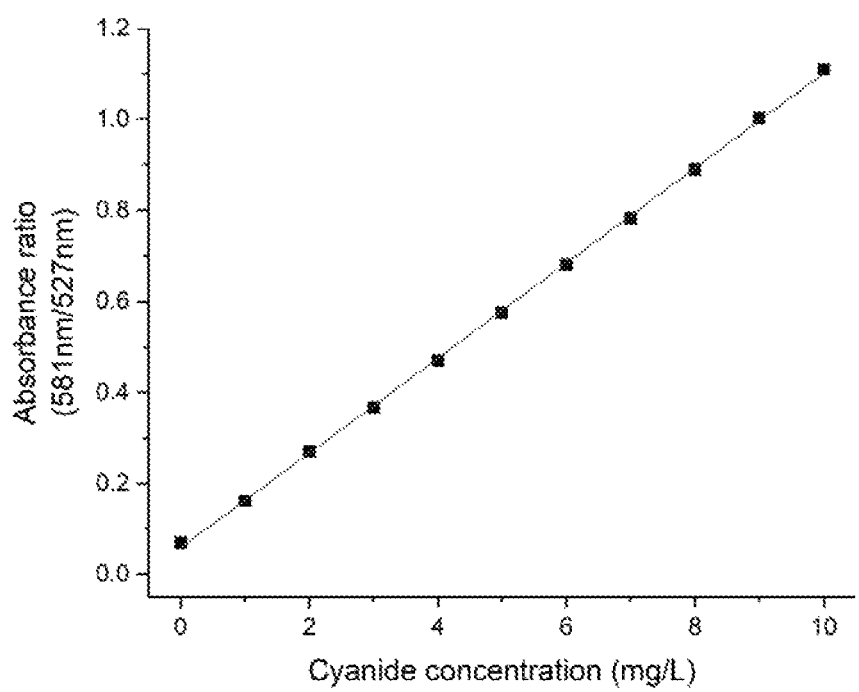
*Cyanide Calibration Curve 581/527 nm*

METHOD OF DETERMINING THE PROPORTION OF CYANIDE IN A SAMPLE

CROSS REFERENCE TO RELATED APPLICATIONS

This application is a national stage application of International Application No. PCT/IB2018/057632, filed Oct. 2, 2018, which claims priority from Great Britain Patent Application No. 1716136.5, filed Oct. 3, 2017, which applications are incorporated herein by reference.

This disclosure relates to the detection of cyanide and to methods for doing so.

Cyanide compounds are essential substances in a variety of industrial applications. A number of industrial processes produce substantial quantities of cyanides. There have been cases of accidental release into the environment, a major problem given the toxicity of cyanides. The problem is compounded by the fact that cyanide pollution is difficult to measure—according to the US EPA, only oil and grease pollution are more difficult. Quick and accurate methods of cyanide detection are therefore very important.

A number of spectroscopic methods have been described for the qualitative analysis of cyanide. Some recent examples for the detection of cyanide in blood are described in papers by Blackledge et al (*Anal. Chem.* 2010, 82, 4216-4221), Zelder et al (*Anal. Methods* 2012, 4.9, 2632-2634) and Swezey et al (J. Analytical Toxicology, 2013, 37, 382-385). However, these do not give quantitative measurements, which must be done by the known laborious methods.

It has now been found that it is possible to make a rapid quantitative determination of cyanide by a quick and reliable method. There therefore provided a method of determining the proportion of cyanide present in a sample, comprising the following steps:
(i) Add the sample to be analysed to a sensor molecule that is selected from cobryrinic acid hepta C1-4 alkyl esters of the Formula I

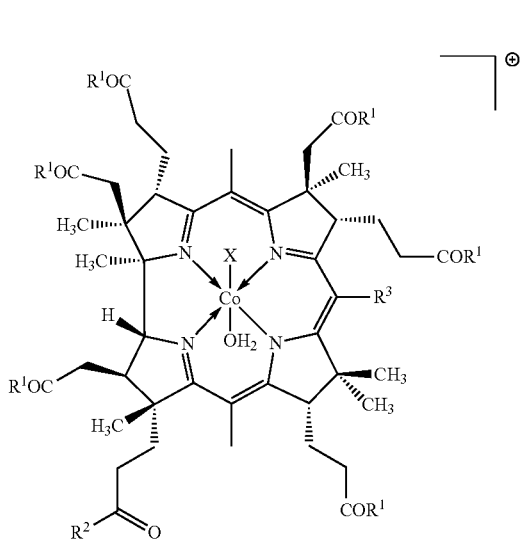

I in which X is CN, $R^3$ is H, and $R^1$ and $R^2$ are $OCH_3$;
(ii) Subject the sample to UV-vis spectroscopic analysis in the range 450-700 nm;
(iii) Determine the free cyanide concentration from the equation (i)

$$C=(A-0.058)/0.104 \quad (i)$$

in which C is the free cyanide concentration and A is the ratio $$A=A_{581}/A_{527}$$

the ratio of the absorbances at 581 and 527 nm, the equation (i) having been derived from a calibration curve that is a plot of A ratios calculated at 0-1 mg/L $CN^-$ with a constant 46 nmol of sensor compound.

The spectroscopic analysis may be carried out using any of the standard types of spectrometer commercially available, for example, the Cary™ 50 spectrometer ex Agilent Technologies. The analyses are carried out in quartz cells with a path length of 1 cm and the UV-vis spectra in the wavelength spectrum between 450-700 nm were measured at T=22±1° C.

The calibration curve was prepared by adding portions of an aqueous 50 mg/L solution of $CN^-$ to a solution of the sensor compound (I) in water, buffered to pH 9.5 with N-cyclohexyl-2-aminoethanesulfonic acid (CHES), starting at 0 mg/L $CN^-$ and moving in 0.1 increments to 1.0 mg/L $CN^-$. The spectrum was taken at each wavelength, the ratio A computed and this ratio plotted against the cyanide concentration (FIG. 1). This curve can then be used to provide the cyanide concentration of an unknown sample.

BRIEF DESCRIPTION OF DRAWINGS

FIG. 1 is a cyanide calibration curve 581/527 nm that can be used to provide the cyanide concentration of an unknown sample.

The sensor molecule of formula I exhibits two absorbance maxima in the 450-700 range at 497 nm and 527 nm. These maxima undergo a bathochromic shift to 538 nm and 581 nm upon binding of a cyanide moiety. The cyanide concentration was calculated using a ratio of absorbance: Abs max of the cyano derivative (581) over Abs max of the sensor compound (527 nm). The absorbance at 581 nm is not sensitive to interferences, while the absorbance at 527 leads to a linear correlation. The use of this ratio allows for better accuracy by removing the concentration dependence (Lambert-Beer law). The ratio of the absorbance values at the wavelengths of about 581 and about 527 nm is then introduced in equation (i) to obtain the free cyanide concentration.

The use of the ratio A, as opposed to the simple absorbance value, is a particular feature of this disclosure. The absorbance is very sensitive to small changes, for example, in the sensor concentration, giving an inaccurate result. The use of the ratio, in conjunction with the particular sensor molecules, overcomes this by removing concentration as a problem. This provides a method that allows a particularly accurate measure of cyanide concentration.

The invention claimed is:
1. A method of determining the proportion of cyanide present in a sample, comprising the following steps:
adding the sample to be analysed to a sensor molecule that is selected from cobryrinic acid hepta C1-4 alkyl esters of the Formula I

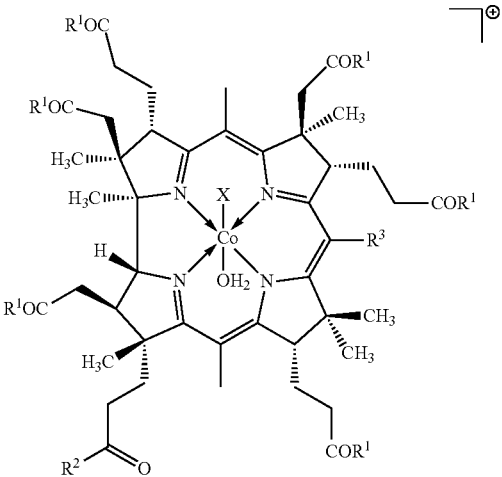

in which X is CN, $R^3$ is H, and $R^1$ and $R^2$ are $OCH_3$;

(ii) subjecting the sample to UV-vis spectroscopic analysis in the range 450-700 nm;

(iii) determining free cyanide concentration from the equation (i)

$$C = (A - 0.058)/0.104 \qquad (i)$$

in which C is the free cyanide concentration and A is $$A = A_{581}/A_{527}$$

the ratio of the absorbances at 581 and 527 nm, wherein 581 nm is the absorbance maxima of a cyano derivative which is the sensor molecule after reaction with cyanide, and 527 nm is the absorbance maxima of the sensor compound, the equation (i) having been derived from a calibration curve that is a plot of A ratios calculated at 0-1 mg/L $CN^-$ with a constant 46 nmol of sensor compound.

\* \* \* \* \*